（12） United States Patent
Barnett et al.

(10) Patent No.: US 11,503,966 B2
(45) Date of Patent: Nov. 22, 2022

(54) SINGLE USE TOWEL DISPENSER WITH STERILIZER AND USAGE LOGGER

(71) Applicant: Sterile Standard, Inc., Northridge, CA (US)

(72) Inventors: Donavin Barnett, Northridge, CA (US); Jonathan Louis Tatkon-Coker, New Brunswick, NJ (US); Raghu Ram Ravuri, Midvale, UT (US)

(73) Assignee: Sterile Standard, Inc., Northridge, CA (US)

( * ) Notice: Subject to any disclaimer, the term of this patent is extended or adjusted under 35 U.S.C. 154(b) by 239 days.

(21) Appl. No.: 16/001,487

(22) Filed: Jun. 6, 2018

(65) Prior Publication Data

US 2019/0374075 A1 Dec. 12, 2019

(51) Int. Cl.
*A47K 10/38* (2006.01)
*A61L 2/10* (2006.01)
(Continued)

(52) U.S. Cl.
CPC ............... *A47K 10/38* (2013.01); *A61L 2/10* (2013.01); *A61L 2/24* (2013.01); *A47K 2010/389* (2013.01); *A61L 2202/11* (2013.01); *A61L 2202/14* (2013.01); *A61L 2202/26* (2013.01); *H04W 4/80* (2018.02)

(58) Field of Classification Search
CPC ..... A47K 10/38; A47K 2010/389; A61L 2/10; A61L 2/24; A61L 2202/11; A61L 2202/14; A61L 2202/26; H04W 4/80
See application file for complete search history.

(56) References Cited

U.S. PATENT DOCUMENTS 6,411,920 B1 6/2002 McConnell et al.
7,044,421 B1 5/2006 Omdoll et al.
(Continued)

FOREIGN PATENT DOCUMENTS

CN 2364887 Y 2/2000
JP 2000037318 A 2/2000
(Continued)

*Primary Examiner* — Regina M Yoo
(74) *Attorney, Agent, or Firm* — Lapple Ubell IP Law, LLP; Matthew C. Lappie

(57) ABSTRACT

A single-use towel dispenser, sterilizer and usage logging device with a refillable storage compartment for storing a single-use towel supply including an access door for refilling the single-use towel supply and a dispensing port, an ultra-violet sterilization element, a single-use towel dispensing mechanism, a user input device, a non-transitory memory storing an executable code and a hardware processor executing the executable code to receive a user input via the user input device, activate, in response to the user input, the ultra-violet sterilization element, dispense, using the single-use towel dispensing mechanism, a sterilized single-use towel by passing a first length of single-use towel from the single-use towel supply within an effective distance of the activated ultra-violet sterilization element such that the first length of single-use towel is illuminated by an ultra-violet light having sufficient intensity to sterilize the first length of single-use towel and store sterilization and usage data in the non-transitory memory.

32 Claims, 9 Drawing Sheets

(51) Int. Cl.
　　　*A61L 2/24*　　　(2006.01)
　　　*H04W 4/80*　　　(2018.01)

(56) References Cited

U.S. PATENT DOCUMENTS

| | | |
|---|---|---|
| 7,370,824 B1 | 5/2008 | Osborne |
| 7,783,380 B2 | 8/2010 | York et al. |
| 7,996,108 B2 | 8/2011 | Yardley |
| 8,297,435 B2 | 10/2012 | Lathem |
| 8,366,035 B2 | 2/2013 | Kling et al. |
| 8,915,422 B1 * | 12/2014 | Harty .................... G06F 3/0416 |
| | | 902/4 |
| 9,271,611 B2 | 3/2016 | Stratmann |
| 9,370,283 B2 | 6/2016 | Fellhoelter |
| 9,398,833 B2 | 7/2016 | Saffran |
| 2013/0240554 A1 | 9/2013 | Stråhlin et al. |
| 2014/0322070 A1 * | 10/2014 | Thomas .................... A61L 2/00 |
| | | 422/1 |
| 2015/0066207 A1 | 3/2015 | Erb |
| 2015/0090832 A1 | 4/2015 | Case et al. |
| 2018/0242577 A1 * | 8/2018 | Tsai ...................... C02F 1/4608 |

FOREIGN PATENT DOCUMENTS

| | | |
|---|---|---|
| KR | 2020120005770 | 2/2011 |
| WO | 2007036130 A1 | 4/2007 |
| WO | 2016122624 A1 | 8/2016 |

* cited by examiner

SINGLE USE TOWEL DISPENSER WITH STERILIZER AND USAGE LOGGER

TECHNICAL FIELD

The present embodiments relate to single use paper towel dispensing devices, paper towel sterilizers, and recordation of paper towel usage. In particular, the present embodiments relate to improvements in a single use paper towel dispenser that uses ultraviolet light to sterilize the single use paper towel as it is being dispensed, and then logs or records that the single use paper towel was dispensed and sterilized to a particular user, at a particular time.

BACKGROUND

Single-use paper towels are used for a wide variety of environments, ranging from home kitchens, to public restrooms, to medical facilities. In certain environments, the fact that a single-use paper towel may have some dust or germs on it is of little consequence. Likewise, in some environments, there is little need to monitor or track the quantity of papers towels used over a period of time.

However, in some sensitive environments, such as hospitals, doctor's offices, children's daycare centers, eldercare centers and tattoo parlors, it can be important and advantageous to ensure that single-use paper towels are dispensed in a sterile condition. Further, it may be important and advantageous to generate a contemporaneous record that each dispensed paper towel was sterilized. Moreover, in such environments, it can be important and advantageous to track paper towel usage. Such usage tracking can be with respect to a number of factors, such as with respect to a particular patient, child, elder or tattoo subject, or by a particular medical procedure or tattoo session, or by a particular doctor, nurse, elder care worker or tattoo artist performing a procedure or job.

It has also been recognized that it may be advantageous to dispense other roll-based materials in a sterilized manner, and to track usage of such materials. For example other roll—based materials include bandages, gauze dressings, and plastic wound sealant, such as a product sold commercially as "Saniderm."

Accordingly, there is a need for a single-use towel dispenser with a sterilizer element and a usage logging capability.

SUMMARY

The various embodiments of the present method and system for a single use towel dispenser with sterilization and usage tracking have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

One aspect of the present embodiments includes the need and ability to ensure that all dispensed single use paper towels are sterilized immediately prior to use and to track the usage of paper towels by a variety of metrics, including but not limited to, tracking by the person dispensing the towel for use, the session in which the towel was dispensed, the patient or subject on whom the paper towel will be used, the date and time of dispensing and the length of time between dispensing separate towels. It would be advantageous, therefore, if a single use paper towel dispenser was capable of sterilization as part of the dispensing operation, and that the paper towel dispenser were capable of tracking, either by itself or in conjunction with a personal computer or server, a wide variety of metrics related to towel usage. The present embodiments provide these advantages and enhancements, as described below.

In a first aspect, a single-use towel dispenser is provided, comprising a refillable storage compartment for storing a single-use towel supply including an access door for refilling the single-use towel supply and a dispensing port, an ultra-violet sterilization element, a single-use towel dispensing mechanism, a user input device, a non-transitory memory storing an executable code and a hardware processor executing the executable code to receive a user input via the user input device, activate, in response to the user input, the ultra-violet sterilization element, dispense, using the single-use towel dispensing mechanism, a sterilized single-use towel by passing a first length of single-use towel from the single-use towel supply within an effective distance of the activated ultra-violet sterilization element such that the first length of single-use towel is illuminated by an ultra-violet light having sufficient intensity to sterilize the first length of single-use towel and store sterilization and usage data in the non-transitory memory.

In an embodiment of the first aspect, the ultra-violet sterilization element is positioned across a first side of the dispensing port.

In another embodiment of the first aspect, the user input device is a button.

In another embodiment of the first aspect, the sterilization data comprises a quantity of single-use towels dispensed, a frequency of single-use towel dispensing, a duration of a sterilization exposure, and an intensity of the sterilization exposure.

In another embodiment of the first aspect, the dispenser further comprises a communication element, where the hardware processor further executes the executable code to transmit, using the communication element, the sterilization data for storage in a remote database.

In another embodiment of the first aspect, the communication element is a wireless communication element.

In another embodiment of the first aspect, the dispensing mechanism is an electric motor connected to a power source.

In another embodiment of the first aspect, the power source is a rechargeable battery.

In another embodiment of the first aspect, the dispenser further comprises a recharging connection for recharging the rechargeable battery.

In another embodiment of the first aspect, the access door for refilling the single-use towel supply is one of a threadably attached end and a hingedly attached door.

In another embodiment of the first aspect, the ultra-violet sterilization element is removable.

In another embodiment of the first aspect, the dispenser further comprises a reflective element positioned across a second side of the dispensing port opposite the first side of the dispensing port such that the sterilized single-use towel dispensed at the dispensing port passes between the sterilization element and the reflective element.

In another embodiment of the first aspect, the hardware processor further executes the executable code to deactivate the ultra-violet sterilization element after dispensing the sterilized single-use towel.

In another embodiment of the first aspect, the sterilization data is recorded during a project time.

In another embodiment of the first aspect, the user input device is one of a mechanical lever, a button, a proximity sensor, and a motion sensor.

In another embodiment of the first aspect, the sterilization and usage data further comprises user identifying data.

In another embodiment of the first aspect, the sterilization and usage data further comprises subject identifying data.

In another embodiment of the first aspect, the sterilization and usage data further comprises the date and time when sterilized towels were dispensed.

In another embodiment of the first aspect, the sterilization and usage data further comprises the number of towels dispensed.

In another embodiment of the first aspect, the sterilization and usage data further comprises the duration and intensity of the UV light generated by the ultra-violet sterilization element each time a towel is dispensed.

In another embodiment of the first aspect, the dispenser further comprises a timer for timing the amount of time elapsed after a towel has been dispensed, an audible alarm, and the audible alarm is configured to be sounded when a predetermined amount of time has elapsed after the towel has been dispensed.

In another embodiment of the first aspect, the predetermined amount of time ranges between a few seconds and up to five minutes.

In another embodiment of the first aspect, the audible alarm is configured to be sounded if fewer than a predetermined number of towels are dispensed at the same time.

In another embodiment of the first aspect, the audible alarm is configured to be sounded if more than a predetermined number of towels are dispensed at the same time.

In a second aspect, a system for dispensing sterilized single use towels and recording data regarding usage is provided, the system comprising a dispenser comprising a refillable storage compartment for storing a single-use towel supply including an access door for refilling the single-use towel supply and a dispensing port, an ultra-violet sterilization element, a single-use towel dispensing mechanism, a user input device, a non-transitory memory storing an executable dispenser device code and a hardware processor executing the executable dispenser device code to receive a user input via the user input device, activate, in response to the user input, the ultra-violet sterilization element, dispense, using the single-use towel dispensing mechanism, a sterilized single-use towel by passing a first length of single-use towel from the single-use towel supply within an effective distance of the activated ultra-violet sterilization element such that the first length of single-use towel is illuminated by an ultra-violet light having sufficient intensity to sterilize the first length of single-use towel and store sterilization and usage data in the non-transitory memory, a transmitter/receiver for operatively communicating with a client device, the client device comprising, a transmitter/receiver, a processor and a memory, where the memory includes executable client device code and a database structure, and where the executable client device code configures the client device to operatively communicate with the dispenser, receive data from the dispenser and store the data in the database structure.

In an embodiment of the second aspect, the client device is a personal computer.

In another embodiment of the second aspect, the client device is a smartphone.

In another embodiment of the second aspect, the data includes sterilization data and usage data.

In another embodiment of the second aspect, the data includes log-in data.

In another embodiment of the second aspect, the executable client device code further configures the client device to enable a user to log-in to the dispenser, using a unique log-in ID, and wherein the executable dispenser device code further configures the dispenser to only dispense a towel after a user has logged-in.

In another embodiment of the second aspect, the operative communication between the dispenser and the client device is via wireless communication.

In another embodiment of the second aspect, the wireless communication is via WiFi.

In another embodiment of the second aspect, the wireless communication is via Bluetooth.

In a third embodiment, a system for dispensing sterilized single use towels and recording data regarding usage is provided, the system comprising a dispenser comprising a refillable storage compartment for storing a single-use towel supply including an access door for refilling the single-use towel supply and a dispensing port, an ultra-violet sterilization element, a single-use towel dispensing mechanism, a user input device, a non-transitory memory storing an executable dispenser device code and a hardware processor executing the executable dispenser device code to receive a user input via the user input device, activate, in response to the user input, the ultra-violet sterilization element, dispense, using the single-use towel dispensing mechanism, a sterilized single-use towel by passing a first length of single-use towel from the single-use towel supply within an effective distance of the activated ultra-violet sterilization element such that the first length of single-use towel is illuminated by an ultra-violet light having sufficient intensity to sterilize the first length of single-use towel and store sterilization and usage data in the non-transitory memory, a transmitter/receiver for operatively communicating with a client device and a server, the client device comprising a transmitter/receiver, a processor and a memory, where the memory includes executable client device code, and the executable client device code enables the client device to operatively communicate with the dispenser and a server and the server is in operative communication with the dispenser and the client device, the server comprising, a processor, a memory, and a database structure stored in the memory, capable of receiving and storing data generated by the dispenser.

In an embodiment of the third aspect, the client device is a personal computer.

In another embodiment of the third aspect, the client device is a smartphone.

In another embodiment of the third aspect, the data includes sterilization data and usage data.

In another embodiment of the third aspect, the data includes log-in data.

In another embodiment of the third aspect, the executable dispenser device code configures the dispenser to only dispense a towel after a user has logged-in and the executable client device code configures the client device to enable a user to log-in to the dispenser, using a unique log-in ID.

In another embodiment of the third aspect, the operative communication between the dispenser and the client device and the server is at least partially via wireless communication.

In another embodiment of the third aspect, the wireless communication is via WiFi.

In another embodiment of the third aspect, the wireless communication is via Bluetooth.

In another embodiment of the third aspect, the server is at a location remote from the dispenser and is in operative communication with the dispenser via the Internet.

In a fourth aspect, a method for use with a single-use towel dispenser including an ultra-violet sterilization element, a non-transitory memory and a hardware processor, is provided, the method comprising receiving a user input from a user input device, activating, in response to the user input, an ultra-violet sterilization element, dispensing, in response to the user input, a sterilized single-use towel by passing a first length of single-use towel from the single-use towel supply within an effective distance of the activated ultra-violet sterilization element such that an entire area of the first length of single-use towel is illuminated by an ultra-violet light having sufficient intensity to sterilize the first length of single-use towel and storing, using the hardware processor, sterilization data including a quantity of single-use towels dispensed, a frequency of single-use towel dispensing, a duration of a sterilization exposure, and an intensity of the sterilization exposure in the non-transitory memory.

In an embodiment of the fourth aspect, the single-use towel dispenser further includes a communication element, and the method further comprises transmitting, using the communication element, the sterilization data for storage in a remote database.

In another embodiment of the fourth aspect, the communication element is a wireless communication element.

In another embodiment of the fourth aspect, the remote database is located in a remote server.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations may have particular advantages not specifically recited in the above summary.

BRIEF DESCRIPTION OF THE DRAWINGS

The various embodiments of the present single-use paper towel dispenser, sterilizer and usage tracker device now will be discussed in detail with an emphasis on highlighting the advantageous features. These embodiments depict the novel and non-obvious single use paper towel dispenser, sterilizer and usage tracker device shown in the accompanying drawings, and the methods which can be performed with them, which are for illustrative purposes only. These drawings include the following figures, in which like numerals indicate like parts.

DETAILED DESCRIPTION

Figure 1:
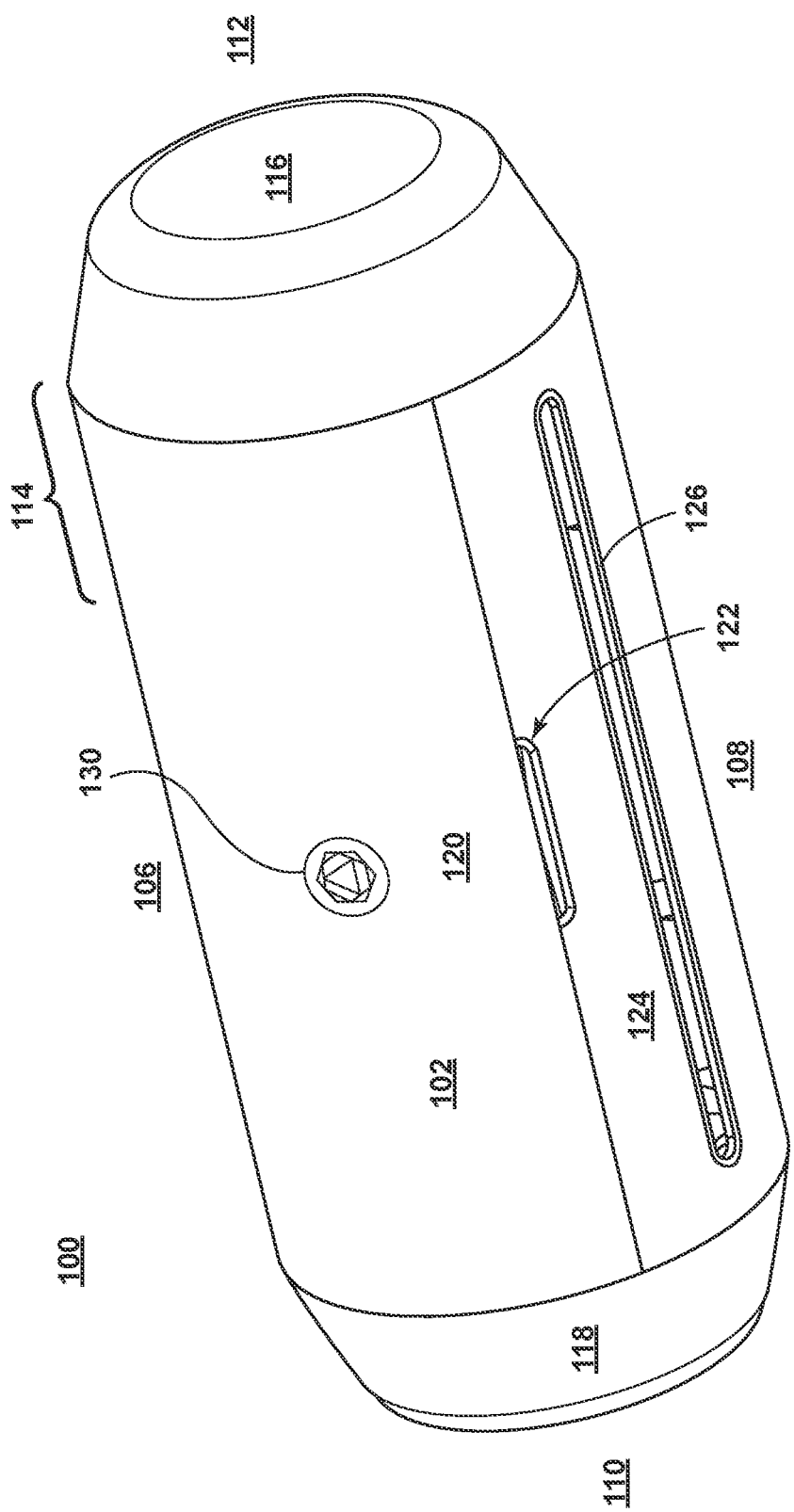
FIG. 1 is bottom front view illustrating a single-use towel dispenser according to various aspects of the present disclosure.

The following detailed description describes the present embodiments with reference to the drawings. In the drawings, reference numbers label elements of the present embodiments. These reference numbers are reproduced below in connection with the discussion of the corresponding drawing features. Whenever the shapes, relative positions and other aspects of the parts described in the embodiments are not explicitly defined, the scope of the invention is not limited only to the parts shown, which are meant merely for the purpose of illustration. Also, while numerous details are set forth, it is understood that some embodiments of the invention may be practiced without these details. In other instances, well-known circuits, structures, and techniques have not been shown in detail so as not to obscure the understanding of this description.

The embodiments of the present method and system for a single use paper towel dispenser, sterilizer and usage tracker device are described below with reference to the figures. These figures, and their written descriptions, indicate that certain components of the apparatus are formed integrally, and certain other components are formed as separate pieces. Those of ordinary skill in the art will appreciate that components shown and described herein as being formed integrally may in alternative embodiments be formed as separate pieces. Those of ordinary skill in the art will further appreciate that components shown and described herein as being formed as separate pieces may in alternative embodiments be formed integrally. Further, as used herein the term integral describes a single unitary piece.

As discussed above, there is a significant need to dispense sterilized single-use paper towels and track and record usage data. For example, it can be advantageous to ensure that all dispensed single use paper towels are sterilized immediately prior to use and to track the usage of paper towels by a variety of metrics, including but not limited to, tracking by the person dispensing the towel for use, the session in which the towel was dispensed, the patient or subject on whom the paper towel will be used, the date and time of dispensing and the length of time between dispensing separate towels. It would be advantageous, therefore, if a single use paper towel dispenser was capable of sterilization as part of the dispensing operation, and that the paper towel dispenser were capable of tracking, either by itself or in conjunction with a personal computer or server, a wide variety of metrics related to towel usage. The present embodiments provide these advantages and enhancements, as described below.

With reference to FIGS. 1-7, the present embodiments include a single use paper towel dispenser, sterilizer and usage tracker device 100, referred to herein as a dispenser. The dispenser 100 has a front 102, a back 104, a top 106, a bottom 108 and two opposed sides 110, 112. The dispenser 100 may be of any reasonable size and dimensions capable of holding an adequately sized motor and spindle for dispensing any given size of roll-based material. FIGS. 1-4 illustrate aspects of the exterior of embodiments of the dispenser 100. The dispenser 100 includes a housing 114 with end caps 116, 118, a door 120, hingedly attached to the housing 114, with an access slot 122 for accessing and opening the door 120, and a dispensing portion 124. The end caps 116, 118 may be affixed to the dispenser by a variety of known means, such as by threads to allow twist-on end caps 116, 118, by snaps, clips, cotter pins, hook-and-eye, tongue-and-and grove connections, and the like. The end caps 116, 118 may also include locking mechanisms (not shown) to enable the end caps to securely hold items to be sterilized at the same time as a single-use towel—or any other roll-based material—is dispensed. Such securely held items could include, for example, a tattoo machine, a tattoo machine bag, a clip cord, clip cord covers, or dental bibs. In certain embodiments, lockable end caps 116, 118 may be referred to as "lock boxes."

Figure 2:
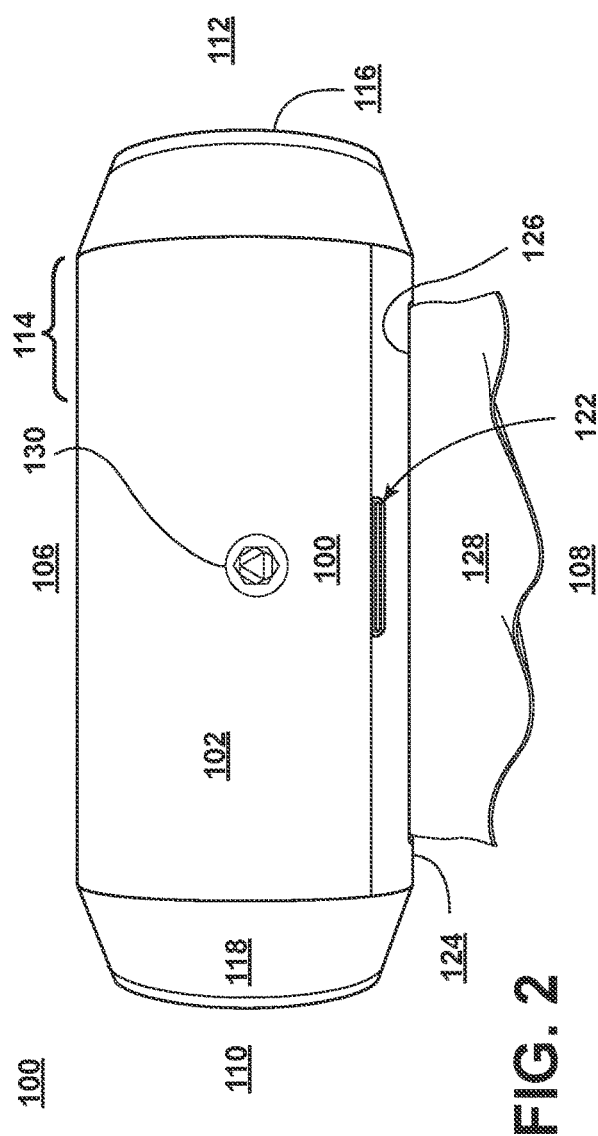
FIG. 2 is a front view illustrating a single-use towel dispenser according to various aspects of the present disclosure.
Figure 4:
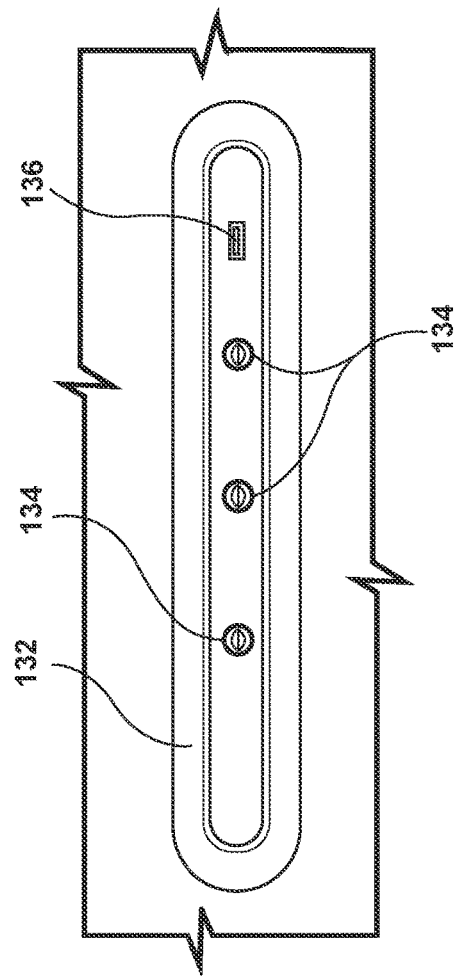
FIG. 4 is a cutaway view of portion of the rear of a single-use towel dispenser according to various aspects of the present disclosure, illustrating connectors and mounting components.
Figure 3:
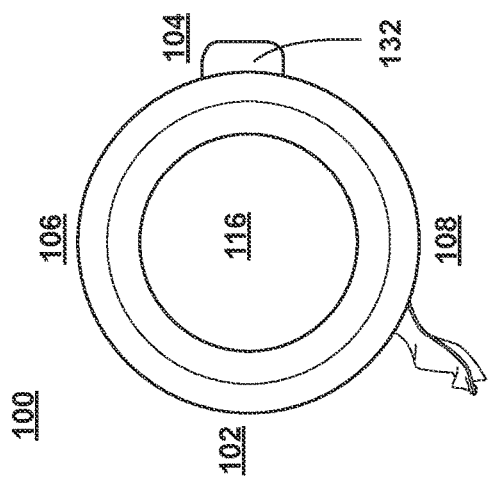
FIG. 3 is right side view illustrating an embodiment of a single-use towel dispenser according to various aspects of the present disclosure.

The dispensing portion 124 includes a dispensing port 126 through which a single-use towel 128 (or other roll-based material) may be dispensed, as shown in FIG. 2. The dispenser 100 has an actuator button 130, which may serve a number of purposes, including as a power button for powering-on the dispenser 100, and as a dispense button, for a user to cause the dispenser 100 to dispense a predetermined length of single-use towel 128, and as an indicator/status/error notification light. The light may be a tri-color light, and may provide status indications for such things as UV light status, WiFi connectivity, Bluetooth connectivity, an empty roll indicator, an error message, and the like.

At the back 104 of the dispenser 100, the dispenser includes a mount 132. The mount 132 may be any generally known type of mount, for mounting a device on a wall, a rack, a table or other work or office surface, or to a base for mounting the dispenser 100. In some embodiments, as shown in close-up in FIG. 4, the mount 132 also includes one or more charging pins 134 for inductive charging. In other embodiments, the mount may include a hidden Qi coil for charging the device. In still other embodiments, the mount may include a micro-Universal Service Bus ("micro-USB") port 136 for charging and communication with other electronic devices with USB capabilities. In still other embodiments, the mount 132 may include terminals for connection to various standard voltages of AC electric power, such as 110-240 volts, or a jack for connection to a specialized DC power supply.

Figure 5:
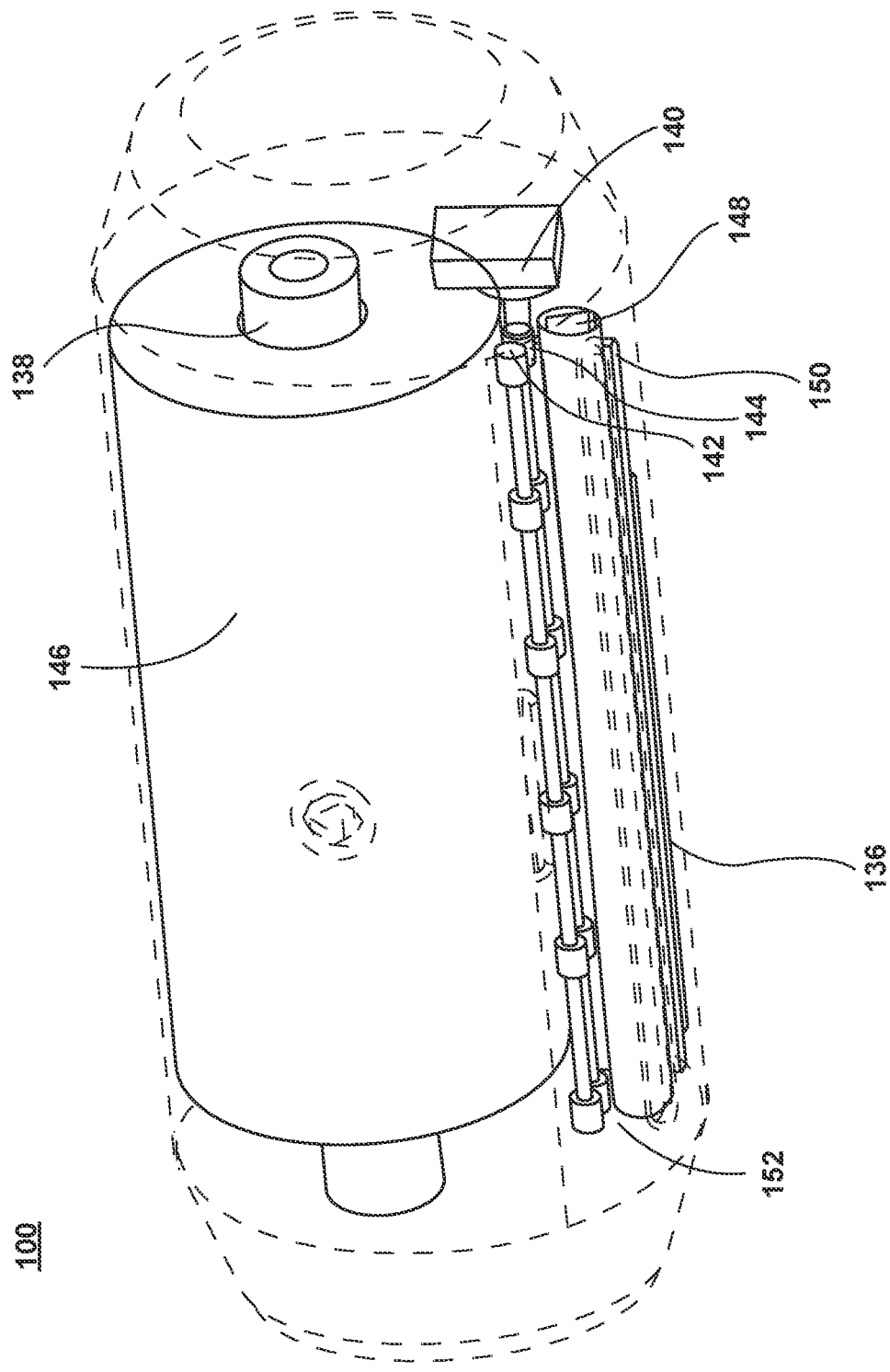
FIG. 5 is a bottom front perspective view, of a single-use towel dispenser, according to various aspects of the present disclosure, with broken lines illustrating the exterior of the dispenser and solid lines illustrating interior components of the dispenser and a roll of paper towels.
Figure 6:
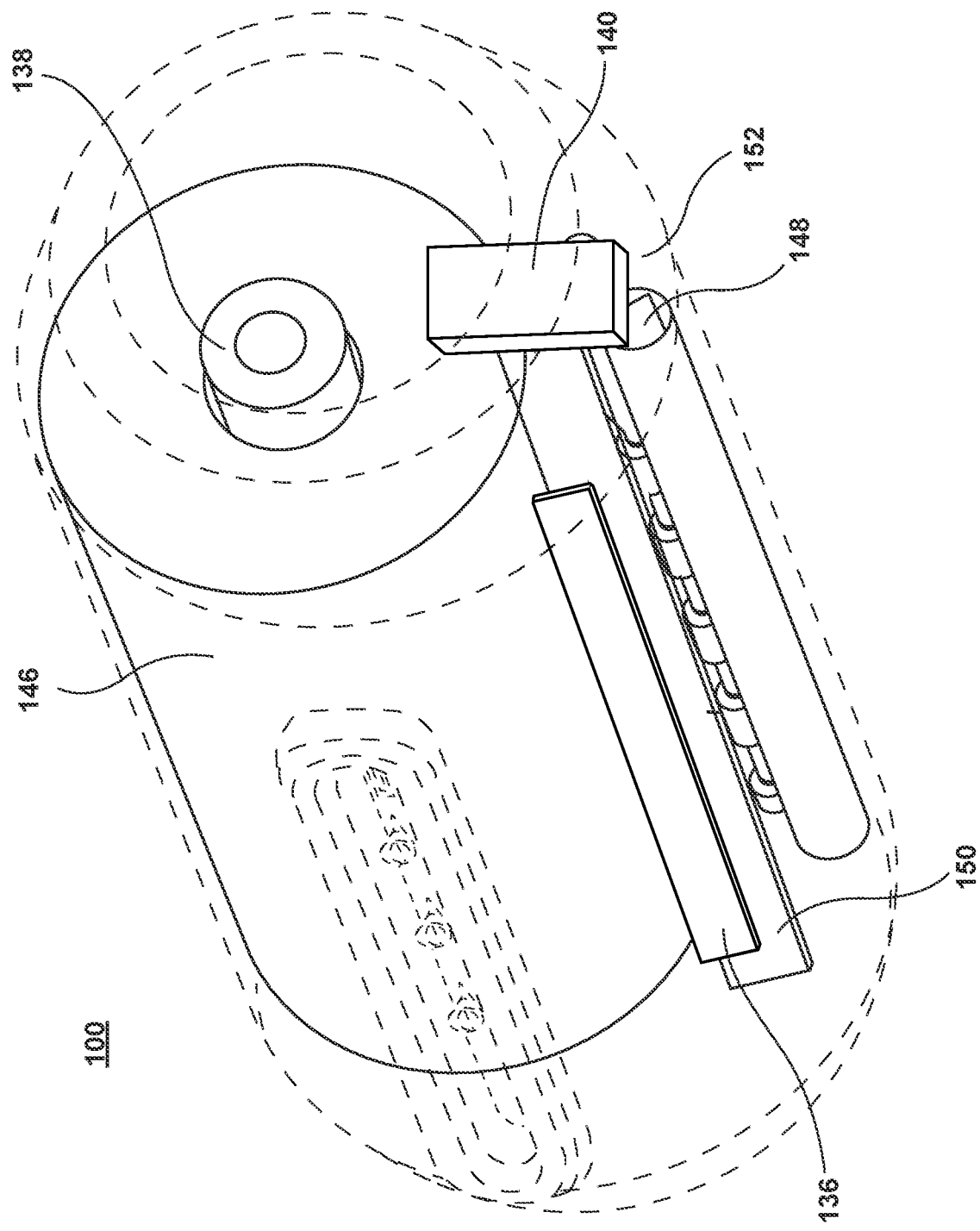
FIG. 6 is bottom rear perspective view, of a single-use towel dispenser, according to various aspects of the present disclosure, with broken lines illustrating the exterior of the dispenser and solid lines illustrating interior components of the dispenser and a roll of paper.
Figure 7:
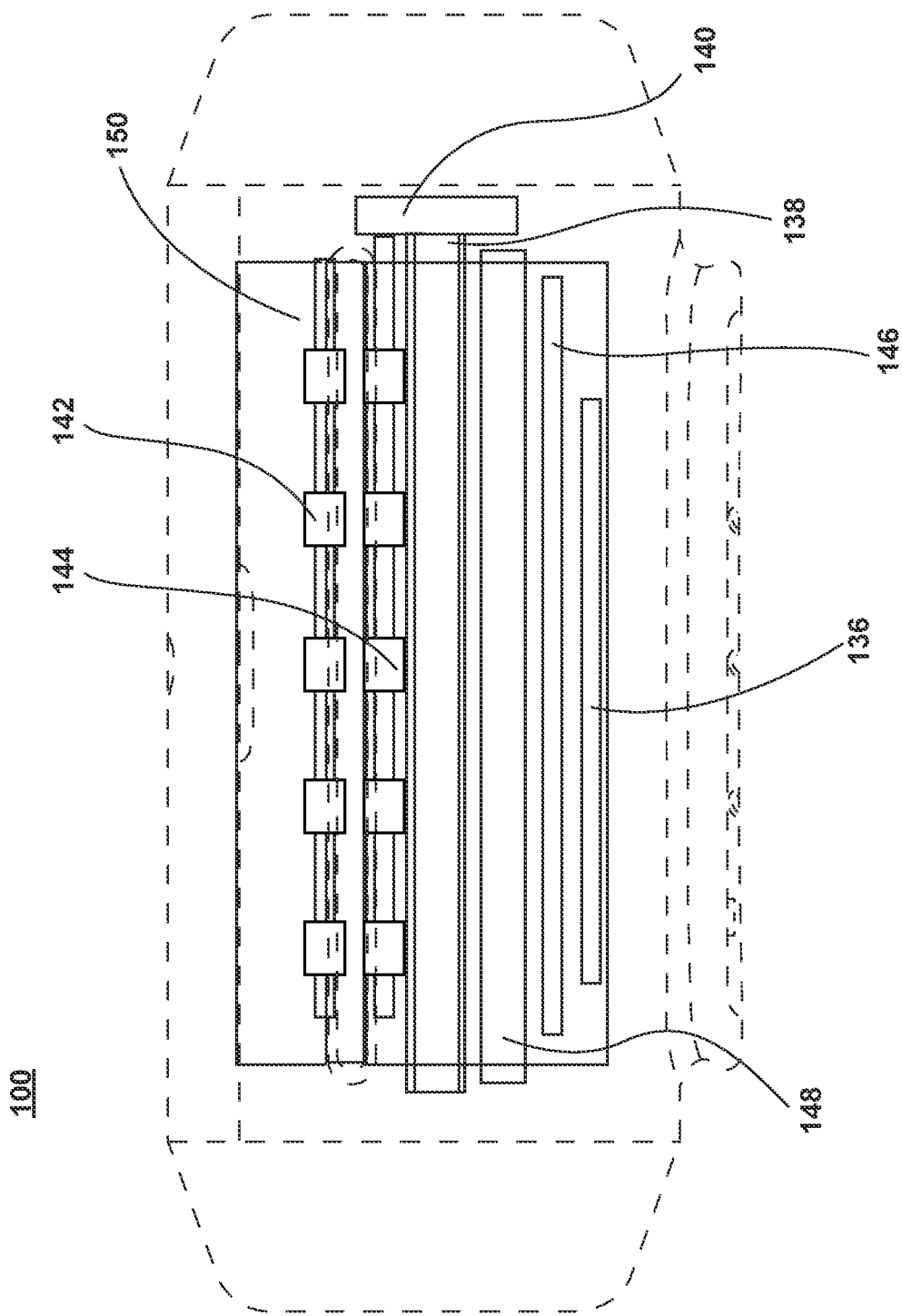
FIG. 7 is a bottom view, of a single-use towel dispenser, according to various aspects of the present disclosure, with broken lines illustrating the exterior of the dispenser and solid lines illustrating interior components of the dispenser.

FIGS. 5-7 illustrate components of the interior of the dispenser 100, and show the housing 114 using phantom lines. The interior components of the dispenser 100 include one or more motors 136, a main spool 138, a drawing spool 140 and dispensing spools 142, 144, each of which are rotatably-mounted in the housing 114. The motors 136, main spool 138, drawing spool 140 and dispensing spools 142, 144 should be understood to be a dispensing mechanism and persons of ordinary skill in the art will appreciate that other configurations and structures for paper towel dispensing exist in the art and may be utilized herein. A continuous web roll 146 of single-use paper towels (or other roll-based materials such as Saniderm) may be removably loaded onto the main spool 138 and a portion of the towel 128 may be fed through the drawing spool 140 and the dispensing spools 142, 144 such that the paper towel 128 may be dispensed through the dispensing port 126. In certain embodiments, the main spool 138 is removable and the roll 146 can be loaded onto the main spool 138 via the hinged access door 120.

The interior components of the dispenser 100 also include sterilization element 148 and printed circuit board (PCB) 150. The sterilization element 148 is preferably an ultraviolet ("UV") light capable of generating UV light of sufficient intensity to destroy and sterilize most commonly known viruses and bacteria. This type of UV light sterilization is also known as "ultraviolet germicidal irradiation" ("UVGI") which is a disinfection method that uses short-wavelength ultra-violet (UV-C) light to kill or inactivate microorganisms by destroying nucleic acids and disrupting their DNA, leaving them unable to perform vital cellular functions. In particular, wavelengths of light around 260-270 nm can kill or disable most microorganisms. The ultra-violet sterilization element 148 is positioned across a first side of the dispensing port 126. In certain embodiments, the sterilization element 148 is oriented close to, and parallel with, the dispensing spools 142, 144, so that the paper towel 128 passes within less than one inch of it, and preferably within a distance of between 1-15 millimeters, so as to ensure a high degree of confidence that the dispensed paper towel 128 has been sterilized.

The sterilization element 148 may be any known UV sterilization device, including a mercury-vapor lamp or a grouping of light-emitting diodes ("LEDs") tuned to a frequency of light between 255-280 nm. In certain embodiments, it is preferred to use UV-LEDs due to their compact size and relatively low power consumption. In some embodiments, the UV sterilization element 148 is removable and replaceable, for cleaning and maintenance. Dust and films that coat a UV bulb, or UV-LEDs, can lower UV output. Therefore, bulbs and some LEDs require periodic cleaning and replacement to ensure effectiveness. The hardware processor discussed further below may be used to activate the sterilization element 148 during a dispensing operation, and further to deactivate the sterilization element 148 after dispensing the sterilized single-use towel 128 is complete. In certain embodiments, the sterilization element 148 is positioned so that its light also reaches the compartments created by the end caps 116, 118, so as to sterilize any devices or materials placed there. In other embodiments, one or more additional sterilization elements (not show) can be mounted so that these additional sterilization elements serve to sterilize the contents of the compartments created by the end caps 116, 118.

In certain embodiments, a reflective element 152 is mounted in the housing 114 to reflect UV light onto the towel 128 as it is being dispensed, or to maximize the intensity of the UV light exposure. The reflective element 152 may be a mirror, polished metal, or other highly reflective surface. The reflective element 152 can be positioned in parallel with the sterilization element 148, along the dispensing port 126 and directly opposite from the sterilization element 148.

The PCB 150 includes a processor and a non-transitory memory, with executable instructions for execution by the processor for controlling the operation of the dispenser 100 and a database structure (or other known memory structure) for storing data generated by the processor. As discussed further herein, the stored data may include date and time stamps, user log-in information, records of when and how many paper towels were dispensed, the frequency of dispensing operations, records that the dispensed paper towels were subjected to a certain intensity of UV light generated by the sterilization element, or that the dispensed paper towels were subjected to the UV light for a certain amount of time, and other readily ascertainable data regarding the performance and status of the dispenser 100. In some embodiments, the PCB 150 includes a communication element. Such a communication element can be a controller for the micro-USB port 136, a WiFi radio chip, a Bluetooth radio chip, other network communication elements discussed herein, or a combination thereof. In such an embodiment, the processor can be configured to execute instructions to control the communication element, or such control can be distributed or localized to the communication element itself.

The dispenser 100 may be directly connected to either DC or AC current, through charging pins 134, the micro-USB port 136, or other electrical connections discussed herein. The dispenser 100 may also include a pair of terminals (not shown) configured to be connected to a source of external AC (alternating-current) power, such as a household AC power supply (may also be referred to as AC mains). The AC power may have a voltage in the range of 16-24 VAC, for example. The incoming AC power may be converted to DC (direct-current) by an AC/DC rectifier (not shown). An output of the AC/DC rectifier may be connected to an input of a DC/DC converter (not shown), which may step down the voltage from the output of the AC/DC rectifier from 16-24 VDC to a lower voltage of about 5 VDC, for example. In various embodiments, the output of the DC/DC converter may be in a range of from about 2.5 V to about 7.5 V, for example. The output of the DC/DC converter may be connected to a power manager, which may comprise an integrated circuit including a processor core, memory, and/or programmable input/output peripherals. In one non-limiting example, the power manager may be an off-the-shelf component, such as the BQ24773 chip manufactured by Texas Instruments. As described in detail below, the power manager controls, among other things, an amount of power drawn from the external AC power supply, as well as an amount of supplemental power drawn from a battery, to power the dispenser 100. The power manager may, for example, limit the amount of power drawn from the external AC power supply so that a threshold power draw is not exceeded. In one non-limiting example, the threshold power, as measured at the output of the DC/DC converter may be equal to 1.4 A. The power manager may also control an amount of power drawn from the external AC power supply and directed to the battery for recharging of the battery. An output of the power manager 140 is connected to a power sequencer, which controls a sequence of power delivery to other components of the dispenser 100, including the communication element, the actuator button 130, the motors 136, the sterilization element 148 and the processor. The power sequencer may comprise an integrated circuit including a processor core, memory, and/or programmable input/ output peripherals. In one non-limiting example, the power sequencer may be an off-the-shelf component, such as the RT5024 chip manufactured by Richtek.

Alternatively, the dispenser 100 may include a rechargeable battery (not shown) for providing power to the PCB 150, motors 136, and sterilization element 148. The battery may comprise, for example, a lithium-ion battery, or any other type of rechargeable battery. The battery may be operably connected to the charging pins 134, micro-USB port 136, inductive Qi coil, AC terminals, or DC terminals, for recharging.

In certain embodiments, the processor may perform data processing and various other functions, as described below. The processor may comprise an integrated circuit including a processor core, memory, non-volatile memory, and/or programmable input/output peripherals (not shown). The memory may comprise, for example, DDR3 (double data rate type three synchronous dynamic random-access memory). The non-volatile memory may comprise, for example, NAND flash memory. The memory and/or the non-volatile memory, regardless of their physical location, may be shared by one or more other components (in addition to the processor) of the present dispenser 100.

The actuator button 130 is operatively connected to the PCB 150. The actuator button 130 may include one or more indicator lights, such as LED lights, to provide status information to a user, such as, for example, showing different light colors or patterns to indicate power-on, network connectivity, dispensing operations, or error codes. In other embodiments, the dispenser 100 may be activated by other types of user input devices, such as a mechanical lever, a proximity sensor, and a motion sensor.

In certain embodiments, the dispenser 100 further includes one or more switches (not shown) in communication with the access door 120 and/or the end caps 116, 118. The switch is operatively connected to the PCB 150 and/or the UV sterilization element 148. When the access door 120 and/or one of the end caps 116, 118 is opened, the switch disables or deactivates the UV sterilization element 148. This serves as a safety feature, to prevent users accidently exposing their eyes or skin to the light generated by the UV sterilization element 148 when the access door 120 is open, or one of the end caps 116, 118 is removed.

Figure 8:
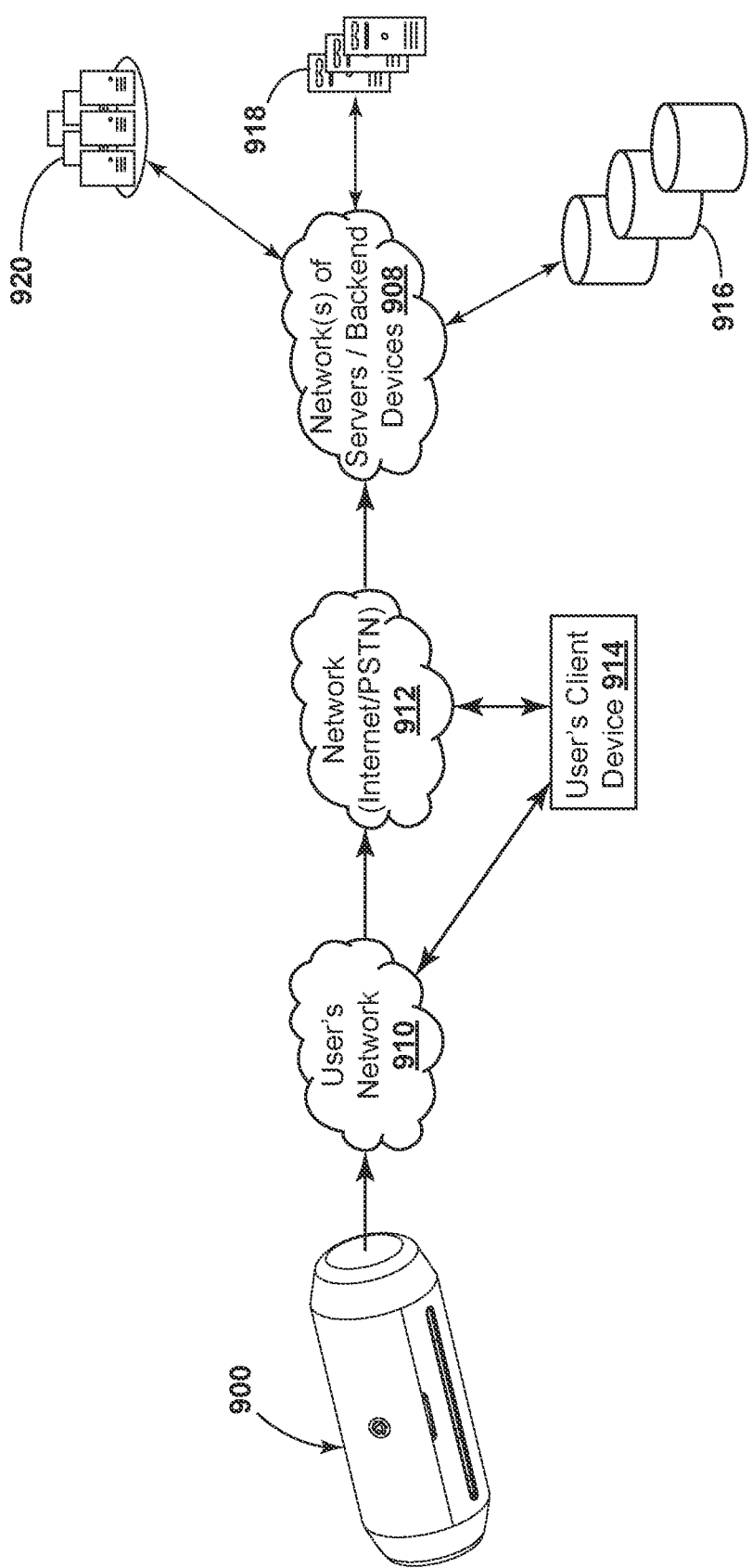
FIG. 8 is a functional block diagram illustrating a system for communicating in a network according to various aspects of the present disclosure.

With reference to FIG. 8, a system that includes a dispenser 900, as discussed herein is illustrated. An embodiment of the single-use towel dispenser 900 communicates with a user's network 910, which may be for example a wired and/or wireless network. If the user's network 910 is wireless, or includes a wireless component, the network 910 may be a Wi-Fi network compatible with the IEEE 802.11 standard, a Bluetooth network, and/or a network based upon another wireless communication standard(s). The user's network 910 is connected to another network 912, which may comprise, for example, the Internet and/or a public switched telephone network (PSTN). As described below, the dispenser 900 may communicate with the user's client device 914 via the network 910 and the network 912 (Internet/PSTN). The user's client device 914 may comprise, for example, a mobile telephone (may also be referred to as a cellular telephone), such as a smartphone, a personal digital assistant (PDA), or another communication device. The user's client device 914 comprises a display (not shown) and related components capable of displaying and inputting data, such as a user log-in, patient/subject data, procedure information (such as "tattoo session"), billing information, or other applicable data. The dispenser 900 may also communicate with one or more remote storage device(s) 916 (may be referred to interchangeably as "cloud storage device(s)"), one or more servers 918, and/or a backend API (application programming interface) 920 via the network 910 and the network 912 (Internet/PSTN). While FIG. 8 illustrates the storage device 916, the server 918, and the backend API 920 as components separate from the network 912 (Internet/PSTN), it is to be understood that the storage device 916, the server 918, and/or the backend API 920 may be considered to be components of the network 912 (Internet/PSTN).

The network 912 (Internet/PSTN) may be any wireless network or any wired network, or a combination thereof, configured to operatively couple the above-mentioned modules, devices, and systems. For example, the network 912 (Internet/PSTN) may include one or more of the following: a PSTN (public switched telephone network), the Internet, a local intranet, a PAN (Personal Area Network), a LAN (Local Area Network), a WAN (Wide Area Network), a MAN (Metropolitan Area Network), a virtual private network (VPN), a storage area network (SAN), a frame relay connection, an Advanced Intelligent Network (AIN) connection, a synchronous optical network (SONET) connection, a digital T1, T3, E1 or E3 line, a Digital Data Service (DDS) connection, a DSL (Digital Subscriber Line) connection, an Ethernet connection, an ISDN (Integrated Services Digital Network) line, a dial-up port such as a V.90, V.34, or V.34bis analog modem connection, a cable modem, an ATM (Asynchronous Transfer Mode) connection, or an FDDI (Fiber Distributed Data Interface) or CDDI (Copper Distributed Data Interface) connection. Furthermore, communications may also include links to any of a variety of wireless networks, including WAP (Wireless Application Protocol), GPRS (General Packet Radio Service), GSM (Global System for Mobile Communication), LTE, VoLTE, LoRaWAN, LPWAN, RPMA, LTE Cat-"X" (e.g. LTE Cat 1, LTE Cat 0, LTE CatM 1, LTE Cat NB1), CDMA (Code Division Multiple Access), TDMA (Time Division Multiple Access), FDMA (Frequency Division Multiple Access), and/or OFDMA (Orthogonal Frequency Division Multiple Access) cellular phone networks, GPS, CDPD (cellular digital packet data), RIM (Research in Motion, Limited) duplex paging network, Bluetooth radio, or an IEEE 802.11-based radio frequency network. The network can further include or interface with any one or more of the following: RS-232 serial connection, IEEE-1394 (Firewire) connection, Fibre Channel connection, IrDA (infrared) port, SCSI (Small Computer Systems Interface) connection, USB (Universal Serial Bus) connection, or other wired or wireless, digital or analog, interface or connection, mesh or Digi® networking.

With further reference to FIG. 8, the server 918 may comprise a computer program and/or a machine that waits for requests from other machines or software (clients) and responds to them. A server typically processes data. One purpose of a server is to share data and/or hardware and/or software resources among clients. This architecture is called the client-server model. The clients may run on the same computer or may connect to the server over a network. Examples of computing servers include database servers, file servers, mail servers, print servers, web servers, game servers, and application servers. The term server may be construed broadly to include any computerized process that shares a resource to one or more client processes. In another example, the network device to which the request is sent may be an API such as the backend API 920, which is described below.

With further reference to FIG. 8, the system may further comprise a backend API 920 including one or more components. A backend API (application programming interface) may comprise, for example, a server (e.g. a real server, or a virtual machine, or a machine running in a cloud infrastructure as a service), or multiple servers networked together, exposing at least one API to client(s) accessing it. These servers may include components such as application servers (e.g. software servers), depending upon what other components are included, such as a caching layer, or database layers, or other components. A backend API may, for example, comprise many such applications, each of which communicate with one another using their public APIs. In some embodiments, the API backend may hold the bulk of the user data and offer the user management capabilities, leaving the clients to have very limited state.

The backend API 920 illustrated FIG. 8 may include one or more APIs. An API is a set of routines, protocols, and tools for building software and applications. An API expresses a software component in terms of its operations, inputs, outputs, and underlying types, defining functionalities that are independent of their respective implementations, which allows definitions and implementations to vary without compromising the interface. Advantageously, an API may provide a programmer with access to an application's functionality without the programmer needing to modify the application itself, or even understand how the application works. An API may be for a web-based system, an operating system, or a database system, and it provides facilities to develop applications for that system using a given programming language. In addition to accessing databases or computer hardware like hard disk drives or video cards, an API can ease the work of programming GUI components. For example, an API can facilitate integration of new features into existing applications (a so-called "plug-in API"). An API can also assist otherwise distinct applications with sharing data, which can help to integrate and enhance the functionalities of the applications.

The backend API 920 illustrated in FIG. 8 may further include one or more services (also referred to as network services). A network service is an application that provides data storage, manipulation, presentation, communication, and/or other capability. Network services are often implemented using a client-server architecture based on application-layer network protocols. Each service may be provided by a server component running on one or more computers (such as a dedicated server computer offering multiple services) and accessed via a network by client components running on other devices. However, the client and server components can both be run on the same machine. Clients and servers may have a user interface, and sometimes other hardware associated with them.

The dispenser 100, 900 can, in certain embodiments, generate, record and/or transfer to a server for recordation, a wide variety of data regarding the access to, use and operation of the dispenser 100, 900. Such data can include, but is not limited to: (a) user identifying data, that identifies the person using the dispenser, e.g., a tattoo artist or a nurse, such user identifying data including but not limited to a user log in, name, identification number or employee number; (b) subject identifying data, that identifies the subject upon whom the towel(s) will be used, e.g. a person being tattooed or a patient, such subject identifying data including a subject name, patient number, or billing ID number; (c) the date and time when sterilized towels were dispensed; (d) the number of towels dispensed; and (e) the duration and intensity of the UV light generated by the ultra-violet sterilization element each time a towel is dispensed; (f) date and time that the roll is changed; and (g) if entered by a user interface on the dispenser or a client device, the brand or materials that were loaded into the device, e.g., paper towels, Saniderm or bandages.

In another embodiment, the dispenser 100, 900 includes a timer for timing the amount of time elapsed after a towel has been dispensed. This timer may be a circuit or software application running on the processor, or may be a separate component. The dispenser 100, 900 may also include an audible alarm, with that audible alarm configured to be sounded when a predetermined amount of time has elapsed after the towel has been dispensed. This predetermined amount of time is adjustable and is ideally the amount of time that it takes for a newly dispensed sterile single-use towel to become contaminated or non-sterile when subjected to the environment where the dispenser 100, 900 is installed. This configuration enables an institution to ensure that a user who dispenses a towel during a procedure, but has not yet used it on a patient, knows that the dispensed towel is likely no longer sterile and no longer safe to use. In certain embodiments, this predetermined amount of time is as little as a few seconds, but in other embodiments can be 1, 2, 3, 4, 5 or up to 10 minutes, or any amount of time within this range. In another embodiment, the audible alarm is configured to be sounded if fewer than a predetermined number of towels are dispensed at the same time. This configuration enables an institution to ensure that a user dispenses a suitable number of towels for the anticipated procedure, and is not undersupplied. In another embodiment, the audible alarm is configured to be sounded if more than a predetermined number of towels are dispensed at the same time. This configuration enables an institution to ensure that a user does not over-dispense and waste towels. In addition to an audible alarm, each of these conditions can be identified, recorded and/or transmitted to a server for recordation, so that the institution or owner of the dispenser may review usage violations of users.

Figure 9:
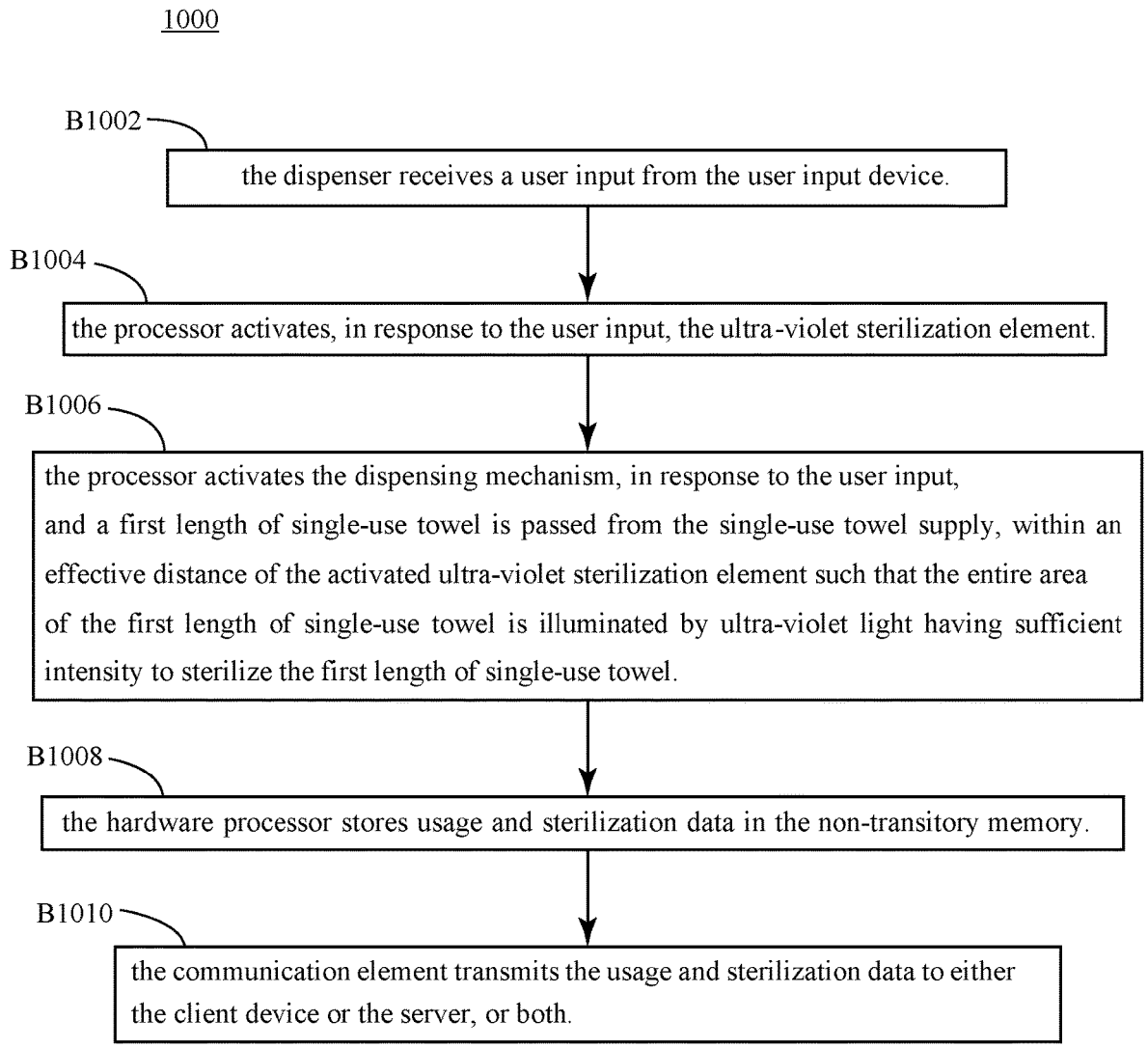
FIG. 9 is a flowchart illustrating an embodiment of a process for using a single-use towel dispenser, to dispense sterilized paper towels and record usage and sterilization data, according to various aspects of the present disclosure.

With reference to FIG. 9, a flowchart is provided illustrating an embodiment of a process 1000 for using a single-use towel dispenser 100, 900, to dispense sterilized paper towels and record usage and sterilization data, according to various aspects of the present disclosure. At block B1002, the dispenser 100, 900 receives a user input from the user input device, such as the actuator button 130. At block B1004, the processor activates, in response to the user input, the ultra-violet sterilization element. At block B1006, the processor activates the dispensing mechanism, in response to the user input such as motion at a motion sensor or pressing the actuator button, and a first length of single-use towel is passed from the single-use towel supply, e.g., the roll 146, within an effective distance of the activated ultra-violet sterilization element 148 such that the entire area of the first length of single-use towel is illuminated by ultra-violet light having sufficient intensity to sterilize the first length of single-use towel. At block B1008, the hardware processor stores usage and sterilization data including, e.g., a quantity of single-use towels dispensed, a frequency of single-use towel dispensing, a duration of a sterilization exposure, and an intensity of the sterilization exposure, in the non-transitory memory. At block B1010, optionally, the communication element transmits the usage and sterilization data to either the client device 914 or the server 908, or both. In a further alternative embodiment, the usage and sterilization data is not stored locally at all, and in simply passed through to the client device 914 or the server 908, or both.

As described above, information processing in the present embodiments may be performed entirely by the dispenser 100, 900, entirely by the client device 914, entirely by one or more backend devices 908, 920, 918, or by a combination of the dispenser 100, 900, the client device 914 and one or more backend devices 908, 920, 918. Moreover, in certain embodiments, the dispenser, client device and backend devices are owned by different entities, bound by contract, while in other embodiments, these components are all owned by the same entity.

In various embodiments, the data generated by the dispenser 100, 900 may be analyzed, organized for reporting by written or electronic means, or categorized so that it may be more useful to the user or institution that installed the dispenser.

Figure 10:
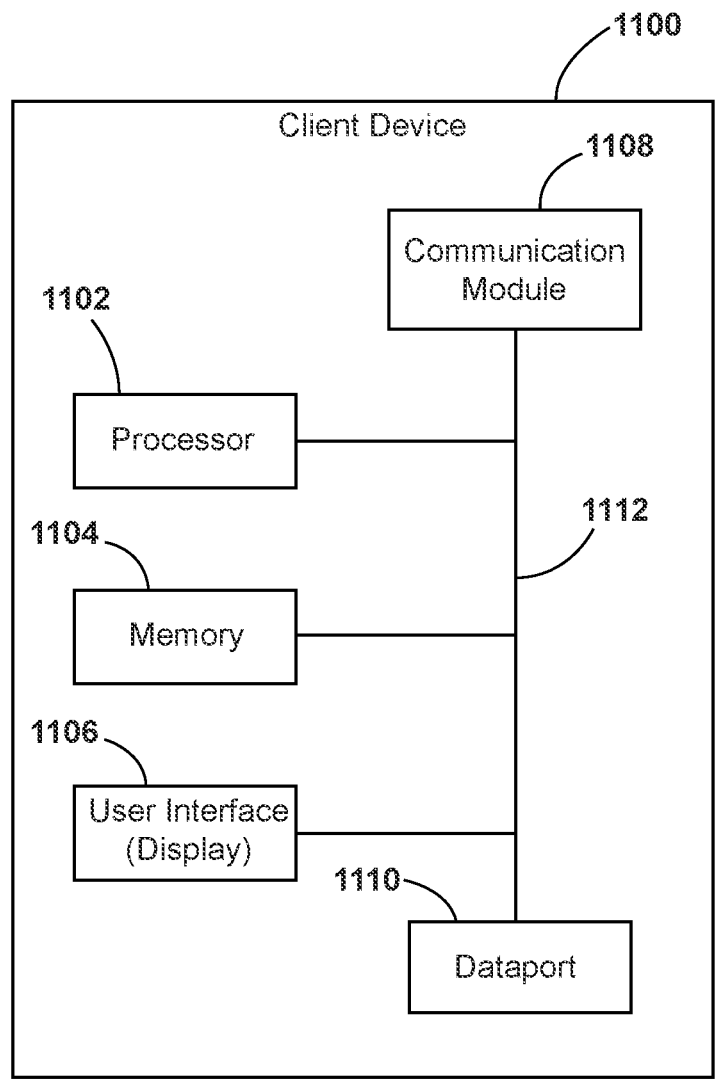
FIG. 10 is a functional block diagram of a client device on which the present embodiments may be implemented according to various aspects of the present disclosure.

FIG. 10 is a functional block diagram of a client device 1100 on which the present embodiments may be implemented according to various aspects of the present disclosure. The user's client device 914 described with reference to FIG. 8 may include some or all of the components and/or functionality of the client device 1100. The client device 1100 may comprise, for example, a smartphone.

With reference to FIG. 10, the client device 1100 includes a processor 1102, a memory 1104, a user interface 1106, a communication module 1108, and a dataport 1110. These components are communicatively coupled together by an interconnect bus 1112. The processor 1102 may include any processor used in smartphones and/or portable computing devices, such as an ARM processor (a processor based on the RISC (reduced instruction set computer) architecture developed by Advanced RISC Machines (ARM).). In some embodiments, the processor 1102 may include one or more other processors, such as one or more conventional microprocessors, and/or one or more supplementary co-processors, such as math co-processors.

The memory 1104 may include both operating memory, such as random access memory (RAM), as well as data storage, such as read-only memory (ROM), hard drives, flash memory, or any other suitable memory/storage element. The memory 804 may include removable memory elements, such as a CompactFlash card, a MultiMediaCard (MMC), and/or a Secure Digital (SD) card. In some embodiments, the memory 1104 may comprise a combination of magnetic, optical, and/or semiconductor memory, and may include, for example, RAM, ROM, flash drive, and/or a hard disk or drive. The processor 1102 and the memory 1104 each may be, for example, located entirely within a single device, or may be connected to each other by a communication medium, such as a USB port, a micro-USB port, a serial port cable, a coaxial cable, an Ethernet-type cable, a telephone line, a radio frequency transceiver, or other similar wireless or wired medium or combination of the foregoing. For example, the processor 1102 may be connected to the memory 1104 via the dataport 1110.

The user interface (Display) 1106 may include any user interface or presentation elements suitable for a smartphone and/or a portable computing device, such as a keypad, a display screen, a touchscreen, a microphone, and a speaker. The communication module 1108 is configured to handle communication links between the client device 1100 and other, external devices or receivers, and to route incoming/outgoing data appropriately. For example, inbound data from the dataport 1110 may be routed through the communication module 1108 before being directed to the processor 1102, and outbound data from the processor 1102 may be routed through the communication module 1108 before being directed to the dataport 1110. The communication module 1108 may include one or more transceiver modules capable of transmitting and receiving data, and using, for example, one or more protocols and/or technologies, such as GSM, UMTS (3GSM), IS-95 (CDMA one), IS-2000 (CDMA 2000), LTE, FDMA, TDMA, W-CDMA, CDMA, OFDMA, Wi-Fi, WiMAX, or any other protocol and/or technology.

The dataport 1110 may be any type of connector used for physically interfacing with a smartphone and/or a portable computing device, such as a mini-USB port or an IPHONE®/IPOD® 30-pin connector or LIGHTNING® connector. In other embodiments, the dataport 1110 may include multiple communication channels for simultaneous communication with, for example, other processors, servers, and/or client terminals.

The memory 1104 may store instructions for communicating with other systems, such as a computer. The memory 1104 may store, for example, a program (e.g., computer program code) adapted to direct the processor 1102 in accordance with the present embodiments. The instructions also may include program elements, such as an operating system. While execution of sequences of instructions in the program causes the processor 1102 to perform the process steps described herein, hard-wired circuitry may be used in place of, or in combination with, software/firmware instructions for implementation of the processes of the present embodiments. Thus, the present embodiments are not limited to any specific combination of hardware and software.

Figure 11:
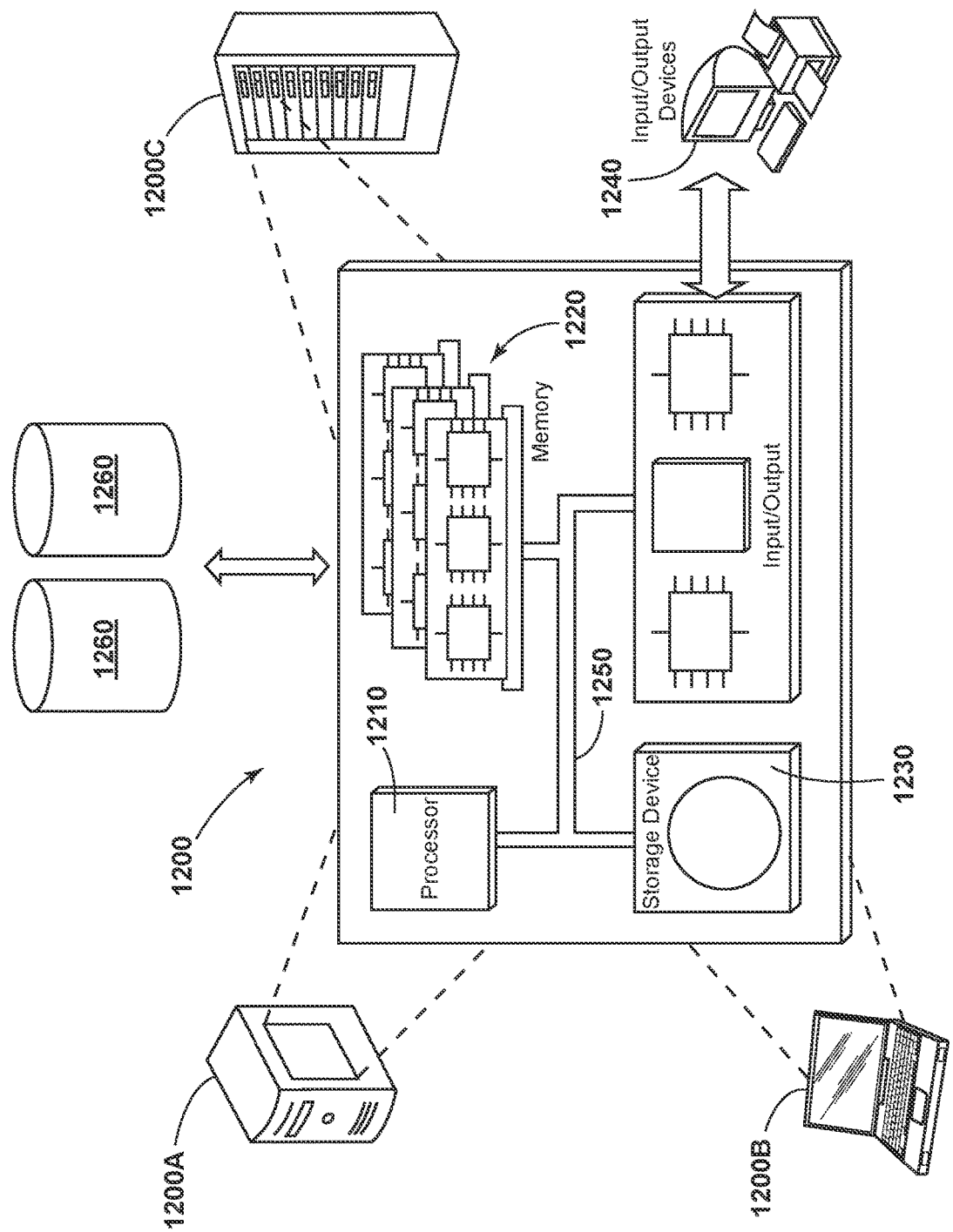
FIG. 11 is a functional block diagram of a general-purpose computing system on which the present embodiments may be implemented according to various aspects of present disclosure.

FIG. 11 is a functional block diagram of a general-purpose computing system on which the present embodiments may be implemented according to various aspects of the present disclosure. The computer system 1200 may be embodied in at least one of a personal computer (also referred to as a desktop computer) 1200A, a portable computer (also referred to as a laptop or notebook computer) 1200B, and/or a server 1200C. A server is a computer program and/or a machine that waits for requests from other machines or software (clients) and responds to them. A server typically processes data. The purpose of a server is to share data and/or hardware and/or software resources among clients. This architecture is called the client-server model. The clients may run on the same computer or may connect to the server over a network. Examples of computing servers include database servers, file servers, mail servers, print servers, web servers, game servers, and application servers. The term server may be construed broadly to include any computerized process that shares a resource to one or more client processes.

The computer system 1200 may execute at least some of the operations described above. The computer system 1200 may include at least one processor 1210, memory 1220, at least one storage device 1230, and input/output (I/O) devices 1240. Some or all of the components 1210, 1220, 1230, 1240 may be interconnected via a system bus 1250. The processor 1210 may be single- or multi-threaded and may have one or more cores. The processor 1210 may execute instructions, such as those stored in the memory 1220 and/or in the storage device 1230. Information may be received and output using one or more I/O devices 1240.

The memory 1220 may store information, and may be a computer-readable medium, such as volatile or non-volatile memory. The storage device(s) 1230 may provide storage for the system 1200, and may be a computer-readable medium. In various aspects, the storage device(s) 1230 may be a flash memory device, a hard disk device, an optical disk device, a tape device, or any other type of storage device.

The I/O devices 1240 may provide input/output operations for the system 1200. The I/O devices 1240 may include a keyboard, a pointing device, and/or a microphone. The I/O devices 1240 may further include a display unit for displaying graphical user interfaces, a speaker, and/or a printer. External data may be stored in one or more accessible external databases 1260.

The features of the present embodiments described herein may be implemented in digital electronic circuitry, and/or in computer hardware, firmware, software, and/or in combinations thereof. Features of the present embodiments may be implemented in a computer program product tangibly embodied in an information carrier, such as a machine-readable storage device, and/or in a propagated signal, for execution by a programmable processor. Embodiments of the present method steps may be performed by a programmable processor executing a program of instructions to perform functions of the described implementations by operating on input data and generating output.

The features of the present embodiments described herein may be implemented in one or more computer programs that are executable on a programmable system including at least one programmable processor coupled to receive data and/or instructions from, and to transmit data and/or instructions to, a data storage system, at least one input device, and at least one output device. A computer program may include a set of instructions that may be used, directly or indirectly, in a computer to perform a certain activity or bring about a certain result. A computer program may be written in any form of programming language, including compiled or interpreted languages, and it may be deployed in any form, including as a stand-alone program or as a module, component, subroutine, or other unit suitable for use in a computing environment.

Suitable processors for the execution of a program of instructions may include, for example, both general and special purpose processors, and/or the sole processor or one of multiple processors of any kind of computer. Generally, a processor may receive instructions and/or data from a read only memory (ROM), or a random access memory (RAM), or both. Such a computer may include a processor for executing instructions and one or more memories for storing instructions and/or data.

Generally, a computer may also include, or be operatively coupled to communicate with, one or more mass storage devices for storing data files. Such devices include magnetic disks, such as internal hard disks and/or removable disks, magneto-optical disks, and/or optical disks. Storage devices suitable for tangibly embodying computer program instructions and/or data may include all forms of non-volatile memory, including for example semiconductor memory devices, such as EPROM, EEPROM, and flash memory devices, magnetic disks such as internal hard disks and removable disks, magneto-optical disks, and CD-ROM and DVD-ROM disks. The processor and the memory may be supplemented by, or incorporated in, one or more ASICs (application-specific integrated circuits).

To provide for interaction with a user, the features of the present embodiments may be implemented on a computer having a display device, such as an LCD (liquid crystal display) monitor, for displaying information to the user. The computer may further include a keyboard, a pointing device, such as a mouse or a trackball, and/or a touchscreen by which the user may provide input to the computer.

The features of the present embodiments may be implemented in a computer system that includes a back-end component, such as a data server, and/or that includes a middleware component, such as an application server or an Internet server, and/or that includes a front-end component, such as a client computer having a graphical user interface (GUI) and/or an Internet browser, or any combination of these. The components of the system may be connected by any form or medium of digital data communication, such as a communication network. Examples of communication networks may include, for example, a LAN (local area network), a WAN (wide area network), and/or the computers and networks forming the Internet.

The computer system may include clients and servers. A client and server may be remote from each other and interact through a network, such as those described herein. The relationship of client and server may arise by virtue of computer programs running on the respective computers and having a client-server relationship to each other.

The above description presents the best mode contemplated for carrying out the present embodiments, and of the manner and process of practicing them, in such full, clear, concise, and exact terms as to enable any person skilled in the art to which they pertain to practice these embodiments. The present embodiments are, however, susceptible to modifications and alternate constructions from those discussed above that are fully equivalent. Consequently, the present invention is not limited to the particular embodiments disclosed. On the contrary, the present invention covers all modifications and alternate constructions coming within the spirit and scope of the present disclosure. For example, the steps in the processes described herein need not be performed in the same order as they have been presented, and may be performed in any order(s). Further, steps that have been presented as being performed separately may in alternative embodiments be performed concurrently. Likewise, steps that have been presented as being performed concurrently may in alternative embodiments be performed separately.

In some embodiments, this disclosure may include the language, for example, "at least one of [element A] and [element B]". This language may refer to one or more of the elements. For example, "at least one of A and B" may refer to "A," "B," or "A and B." Specifically, "at least one of A and B" may refer to "at least one of A and at least one of B," or "at least one of either A or B." In some embodiments, this disclosure may include the language, for example, "[element A], [element B], and/or [element C]." This language may refer to either of the elements or any combination thereof. For instance, "A, B, and/or C" may refer to "A," "B," "C," "A and B," "A and C," "B and C," or "A, B, and C".

What is claimed is:

1. A system for dispensing sterilized single use towels and recording data regarding sterilization and usage comprising:
    a dispenser and a client device, wherein the dispenser and the client device are in operative communication;
    the dispenser comprising:
        a refillable storage compartment for storing a roll of continuous web single-use towels on a main spool, including an access door for refilling the roll of continuous web single-use towels and a dispensing port;
        a single ultra-violet sterilization light positioned adjacent to and parallel with the dispensing port;
        a single-use towel dispensing mechanism comprising a motor, the main spool and a draw spool, configured to rotate the main spool and dispense a single-use towel from the roll of continuous web single-use towels through the dispensing port;
        a user input button;
        a non-transitory memory storing an executable dispenser device code; and
        a hardware processor executing the executable dispenser device code to:
            receive a user input via the user input button or via the client device;
            activate, in response to the user input, the single ultra-violet sterilization light;
            dispense, using the single-use towel dispensing mechanism, a sterilized single-use towel by activating the motor to drive the draw spool such that the main spool is rotated and a single-use towel is passed within a distance of less than one inch of the activated single ultra-violet sterilization light such that the single-use towel is illuminated by radiation from the single ultra-violet sterilization light having sufficient intensity to sterilize the single-use towel, and then out through the dispensing port;
            store sterilization and usage data in the non-transitory memory;
            a transmitter/receiver for operatively communicating with the client device;
    the client device comprising:
        a transmitter/receiver;
        a processor;
        a memory; and
            wherein the memory includes executable client device code and a database structure;
            wherein the executable client device code configures the client device to:
                operatively communicate with the dispenser;
                receive sterilization and usage data from the dispenser; and
                store the data in the database structure.

2. The system of claim 1, wherein the client device is a personal computer.

3. The system of claim 1, wherein the client device is a smartphone.

4. The system of claim 1, wherein the data includes log-in data.

5. The system of claim 1, wherein the executable client device code further configures the client device to enable a user to log-in to the dispenser, using a unique log-in ID, and wherein the executable dispenser device code further configures the dispenser to only dispense a towel after a user has logged-in.

6. The system of claim 1, wherein the operative communication between the dispenser and the client device is via wireless communication.

7. The system of claim 6, wherein the wireless communication is via WiFi.

8. The system of claim 6, wherein the wireless communication is via Bluetooth.

9. The system of claim 1, wherein the single ultra-violet sterilization light is a plurality of light emitting diodes.

10. The system of claim 1, wherein the single ultra-violet sterilization light is an ultraviolet light emitting bulb.

11. The system of claim 1, wherein the refillable storage compartment further comprises:
    a lock box for storage of implements;
    wherein the lock box is positioned and configured such that an interior of the lock box is exposed to the radiation from the single ultra-violet sterilization light, such that when implements are stored in the lock box, the implements are exposed to the radiation from the single ultra-violet sterilization light sufficient to sterilize the implements.

12. The system of claim 1, wherein the refillable storage compartment further comprises:
a rechargeable battery, operatively connected to the motor, the ultra-violet sterilization light, the non-transitory memory, the hardware processor, and the transmitter/receiver of the dispenser;
an inductive charging element, operatively linked to the rechargeable battery, for charging the rechargeable battery.

13. The system of claim 12, wherein the inductive charging element comprises a Qi coil.

14. The system of claim 1, further comprising:
a disabling switch, in communication with the access door and the single ultra-violet sterilization light;
wherein when the access door is open, the disabling switch prevents activation of the single ultra-violet sterilization light.

15. The system of claim 1 wherein the distance of less than one inch comprises between 1-15 millimeters.

16. The system of claim 1 further comprising:
wherein the single ultra-violet sterilization light is positioned across a first side of the dispensing port;
a reflective element;
wherein the reflective element is positioned across a second side of the dispensing port opposite the first side of the dispensing port;
wherein the single-use towel has a first surface and a second surface;
such that the single-use towel dispensed at the dispensing port passes between the single ultra-violet sterilization light and the reflective element;
whereby a first quantity of radiation emitted by the single ultra-violet sterilization light will strike the first surface of the single-use towel.

17. A system for dispensing sterilized single-use towels and recording sterilization and data regarding usage comprising:
a dispenser, a client device, and a server wherein the dispenser, the client device, and the server are in operative communication;
the dispenser comprising:
a refillable storage compartment for storing a roll of continuous web single-use towels on a main spool, including an access door for refilling the roll of continuous web single-use towels, and a dispensing port;
a single ultra-violet sterilization light positioned adjacent to and parallel with the dispensing port;
a single-use towel dispensing mechanism, comprising a motor, the main spool and a draw spool, configured to rotate the main spool and dispense a single-use towel from the roll of continuous web single-use towels through the dispensing port;
a user input button;
a non-transitory memory storing an executable dispenser device code; and
a hardware processor executing the executable dispenser device code to:
receive a user input via the user input button or via the client device;
activate, in response to the user input, the single ultra-violet sterilization light;
dispense, using the single-use towel dispensing mechanism, a sterilized single-use towel by activating the motor to drive the draw spool such that the main spool is rotated and a single-use towel is passed within a distance of less than to one inch from the single ultra-violet sterilization light having sufficient intensity to sterilize the single-use towel, and then out through the dispensing port; and
store sterilization and usage data in the non-transitory memory;
a transmitter/receiver for operatively communicating with the client device and the server;
the client device comprising:
a transmitter/receiver;
a processor;
a memory; and
wherein the memory includes executable client device code;
wherein the executable client device code enables the client device to operatively communicate with the dispenser and the server; and
the server comprising:
a processor;
a memory;
a database structure stored in the memory, capable of receiving and storing sterilization and usage data generated by the dispenser.

18. The system of claim 17, wherein the client device is a personal computer.

19. The system of claim 17, wherein the client device is a smartphone.

20. The system of claim 17, wherein the data includes log-in data.

21. The system of claim 17, wherein the executable dispenser device code configures the dispenser to only dispense a single-use towel after a user has logged-in; and the executable client device code configures the client device to enable a user to log-in to the dispenser, using a unique log-in ID.

22. The system of claim 17, wherein the operative communication between the dispenser and the client device and the server is at least partially via wireless communication.

23. The system of claim 22, wherein the wireless communication is via WiFi.

24. The system of claim 22, wherein the wireless communication is via BlueTooth.

25. The system of claim 17, wherein the server is at a location remote from the dispenser and is in operative communication with the dispenser via the Internet.

26. The system of claim 17, wherein the single ultra-violet sterilization light is a plurality of light emitting diodes.

27. The system of claim 17, wherein the single ultra-violet sterilization light is an ultra-violet light emitting bulb.

28. The system of claim 17, wherein the refillable storage compartment further comprises:
a lock box for storage of implements;
wherein the lock box is positioned and configured such that an interior of the lock box is exposed to the radiation from the single ultra-violet sterilization light, such that when implements are stored in the lock box, the implements are exposed to the radiation from the single ultra-violet sterilization light sufficient to sterilize the implements.

29. The system of claim 17, wherein the refillable storage compartment further comprises:
a rechargeable battery, operatively connected to the motor, the ultra-violet sterilization light, the non-transitory memory, the hardware processor, and the transmitter/receiver of the dispenser;
an inductive charging element, operatively linked to the rechargeable battery, for charging the rechargeable battery.

30. The system of claim 29, wherein the inductive charging element comprises a Qi coil.

31. The system of claim 17 wherein the distance of less than one inch comprises between 1-15 millimeters.

32. The system of claim 17 further comprising:
wherein the single ultra-violet sterilization light is positioned across a first side of the dispensing port;
a reflective element;
wherein the reflective element is positioned across a second side of the dispensing port opposite the first side of the dispensing port;
wherein the single-use towel has a first surface and a second surface;
such that the single-use towel dispensed at the dispensing port passes between the single ultra-violet sterilization light and the reflective element;
whereby a first quantity of radiation emitted by the single ultra-violet sterilization light will strike the first surface of the single-use towel.

* * * * *